(12) United States Patent
Castan et al.

(10) Patent No.: US 11,549,091 B2
(45) Date of Patent: Jan. 10, 2023

(54) BIOREACTOR WITH ADDITION TUBE

(71) Applicant: Cytiva Sweden AB, Uppsala (SE)

(72) Inventors: Andreas Castan, Uppsala (SE); Klaus Gebauer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 927 days.

(21) Appl. No.: 14/910,824

(22) PCT Filed: Aug. 27, 2013

(86) PCT No.: PCT/SE2013/051001
§ 371 (c)(1),
(2) Date: Feb. 8, 2016

(87) PCT Pub. No.: WO2015/030639
PCT Pub. Date: Mar. 5, 2015

(65) Prior Publication Data
US 2016/0194591 A1  Jul. 7, 2016

(51) Int. Cl.
*C12M 1/00* (2006.01)
*C12M 1/06* (2006.01)
(Continued)

(52) U.S. Cl.
CPC ............ *C12M 29/00* (2013.01); *C12M 21/08* (2013.01); *C12M 23/14* (2013.01); *C12M 23/26* (2013.01);
(Continued)

(58) Field of Classification Search
CPC ...... C12M 23/14; C12M 23/26; C12M 23/38; C12M 27/02; C12M 27/16; C12M 29/00; C12M 21/08; C12M 29/14; C12N 1/16; C12N 1/20; C12N 5/04; C12N 5/0601; C12N 5/0602
See application file for complete search history.

(56) References Cited

U.S. PATENT DOCUMENTS 4,713,345 A * 12/1987 Ramsden ............... C12M 23/08
435/261
5,832,973 A    11/1998 Goldschmidt et al.
(Continued)

FOREIGN PATENT DOCUMENTS

CN    101909758 A    12/2010
CN    102892487 A    1/2013
(Continued)

OTHER PUBLICATIONS

International Search Report and Written Opinion regarding International Application No. PCT/SE2013/051001, dated Apr. 25, 2014, 10 pages.
(Continued)

*Primary Examiner* — Liban M Hassan
(74) *Attorney, Agent, or Firm* — Eversheds Sutherland (US) LLP

(57) ABSTRACT

The invention discloses a bioreactor with a vessel defining an inner volume, agitation means and at least one addition tube, wherein a delivery orifice in the addition tube is located within the inner volume and a check valve is arranged in proximity of the delivery orifice for allowing flow of a fluid in the direction from the addition tube into the inner volume of the vessel and blocking flow in the reverse direction.

11 Claims, 7 Drawing Sheets

(51) Int. Cl.

| | | |
|---|---|---|
| *C12M 3/00* | (2006.01) | |
| *C12M 3/06* | (2006.01) | |
| *C12N 1/16* | (2006.01) | |
| *C12N 1/20* | (2006.01) | |
| *C12N 5/04* | (2006.01) | |
| *C12N 5/07* | (2010.01) | |
| *C12N 5/071* | (2010.01) | |

(52) U.S. Cl.
CPC .......... *C12M 23/38* (2013.01); *C12M 27/02* (2013.01); *C12M 27/16* (2013.01); *C12M 29/14* (2013.01); *C12N 1/16* (2013.01); *C12N 1/20* (2013.01); *C12N 5/04* (2013.01); *C12N 5/0601* (2013.01); *C12N 5/0602* (2013.01)

(56) References Cited

U.S. PATENT DOCUMENTS

| | | |
|---|---|---|
| 9,060,538 B2 | 6/2015 | Endo et al. |
| 9,550,969 B2 | 1/2017 | Chotteau et al. |
| 2002/0053537 A1 | 5/2002 | Lucido et al. |
| 2006/0270036 A1 | 11/2006 | Goodwin et al. |
| 2009/0311776 A1 | 12/2009 | Kelly, Jr. et al. |
| 2010/0261226 A1 | 10/2010 | Niazi |
| 2011/0038222 A1* | 2/2011 | Ludwig et al. ..... B01F 3/04269 366/102 |
| 2011/0111486 A1 | 5/2011 | Furey |
| 2011/0223581 A1* | 9/2011 | Stobbe .................. C12M 23/34 435/3 |
| 2012/0028325 A1 | 2/2012 | Herring et al. |
| 2012/0122164 A1* | 5/2012 | El-Shafie ................. C02F 3/34 435/134 |
| 2013/0005010 A1 | 1/2013 | Bell et al. |

FOREIGN PATENT DOCUMENTS

| | | |
|---|---|---|
| DE | 202005014713 U1 | 1/2006 |
| DE | 102011050623 A1 | 11/2012 |
| EP | 2517577 A1 | 10/2012 |
| EP | 2586857 A1 | 5/2013 |
| EP | 2686415 A1 | 1/2014 |
| EP | 3039115 A1 | 7/2016 |
| JP | 02117364 A | 5/1990 |
| JP | 3009386 U | 4/1995 |
| JP | 8-84980 A | 4/1996 |
| JP | 2001046015 A | 2/2001 |
| JP | 5923529 B2 | 5/2016 |
| WO | 02098800 A1 | 12/2002 |
| WO | 2010/008578 A2 | 1/2010 |
| WO | 2011078324 A1 | 6/2011 |
| WO | 2012/097079 A2 | 7/2012 |
| WO | 2012128703 A1 | 9/2012 |
| WO | 2012167179 A1 | 12/2012 |
| WO | 2015/030639 A1 | 3/2015 |

OTHER PUBLICATIONS

Office Action Received for Japanese Patent Application No. 2016-538889, dated Jun. 22, 2017, 9 Pages (4 Pages English Translation + 5 Pages official Copy).

International Preliminary Report on Patentability Received for PCT Application No. PCT/SE2013/051001 dated Mar. 1, 2016, 6 Pages.

Chinese Search Report Received for Chinese Patent Application No. 201380079166.0, dated Feb. 23, 2017 (2 pages of English translation).

Extended European Search Report Received for European Patent Application No. 13892309.9, dated Mar. 24, 2017, 8 pages.

WPI, "Database WPI", Week 201364,Thomson Scientific, 2013, 2 Pages.

Lambda Minofor, Laboratory Fermenter-Bioreactor Operation Manual, 93 pages.

MiniValve Product Sheet, https://web.archive.org/web/20120630062906/ http://www.minivalve.com:80/ (1 page).

European Patent Office Communication of a Notice of Opposition for EP Patent No. 3039115 dated Mar. 18, 2020 (33 pages).

Response to Notice of Opposition for EP Patent No. 3039115 dated Aug. 4, 2020 (59 pages).

\* cited by examiner

BIOREACTOR WITH ADDITION TUBE

CROSS REFERENCE TO RELATED APPLICATIONS

This application is a filing under 35 U.S.C. 371 of international application number PCT/SE2013/051001, filed Aug. 27, 2013, the entire disclosure of which is hereby incorporated by reference.

TECHNICAL FIELD OF THE INVENTION

The present invention relates to bioreactors, and more particularly to addition tubes for bioreactors. The invention also relates to cultivation of cells in bioreactors with addition tubes.

BACKGROUND OF THE INVENTION

In the biopharmaceutical and Life Sciences industries, cells are commonly cultivated with the purpose either to recover products expressed by the cells, such as proteins, vaccine components etc. or to recover e.g. stem cells for therapeutic use. The cultivation conditions need to be carefully controlled and it is common practice to add reagents such as pH regulators, gases, nutrients, antifoam etc. to the culture during cultivation. This is done by pumping through an addition tube, which can have a delivery orifice (usually the end of the tube) either immersed in the cell culture medium or suspended above the cell culture medium. The pump is typically run intermittently, either controlled by a feedback loop or by a fixed addition program. One issue is then that reagent may be delivered by dripping or diffusion even when the pump is stopped, causing poor control of the reagent supply. When the delivery orifice is immersed, a further issue is also that cell culture medium and cells may enter the tube and be subjected to highly toxic conditions leading to cell death and release of detrimental signal substances. When the delivery orifice is suspended above the medium, the reagent may also go primarily into the foam layer on top of the medium, preventing proper distribution in the culture.

Accordingly there is a need for a well-controlled method of adding reagents to a cell culture with no risk of cells being subjected to overly high local reagent concentrations.

SUMMARY OF THE INVENTION

One aspect of the invention is to provide a bioreactor for well-controlled addition of reagents to cell cultures.

One advantage is that reagents are only delivered when intended and in the amounts intended. Further advantages are that the reagents are evenly distributed and that cells are not exposed locally to high transient reagent concentrations.

Another aspect of the invention is to provide a method of cultivating cells with well-controlled addition of reagents. This is achieved with a cell cultivation method as defined in the claims.

Further suitable embodiments of the invention are described in the dependent claims.

DETAILED DESCRIPTION OF EMBODIMENTS

Figure 1:
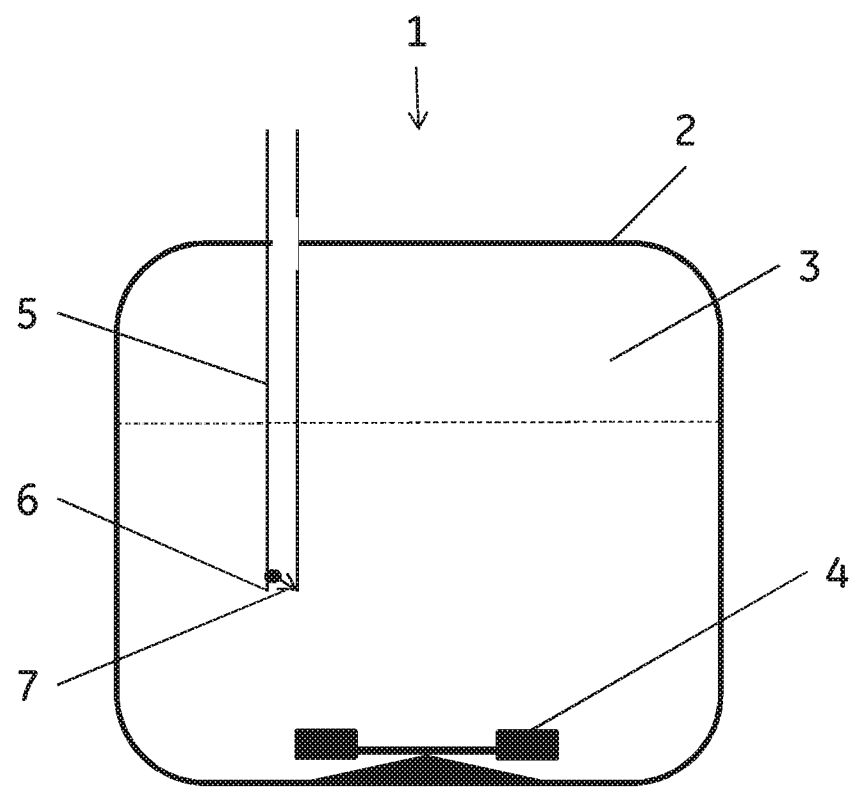
FIG. 1 shows a bioreactor according to the invention.
Figure 2:
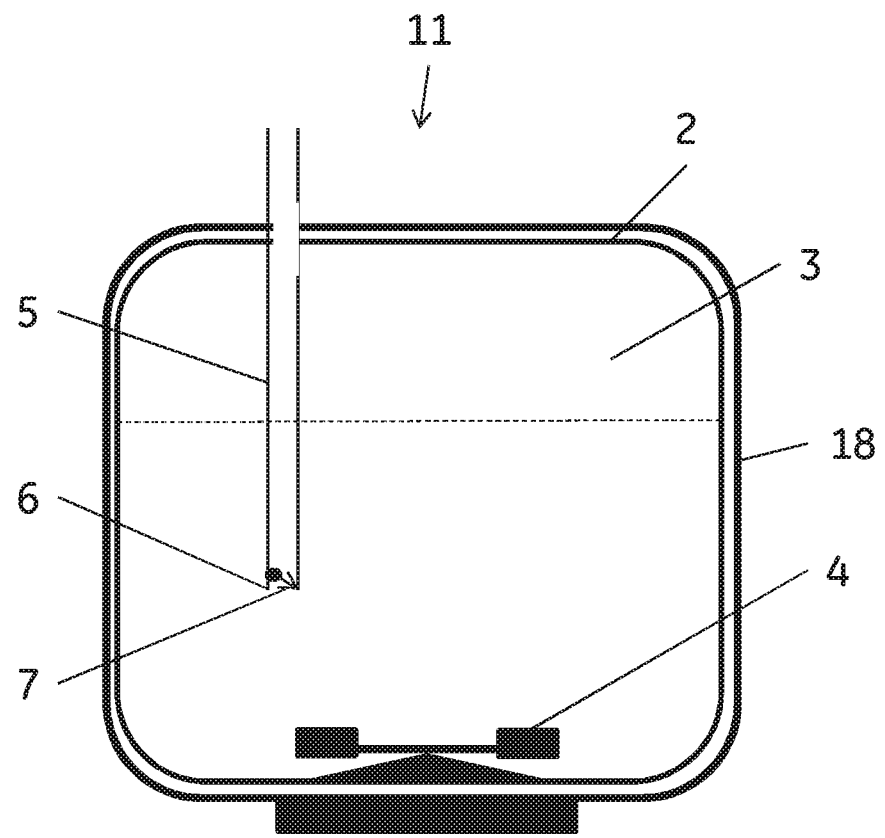
FIG. 2 shows a bioreactor according to the invention, with a plastic bag supported by a rigid structure.

In one aspect the present invention discloses a bioreactor 1;11;21 comprising a vessel 2;22 which defines an inner volume 3;23. The bioreactor further comprises agitation means 4;24 and at least one addition tube 5;25, where a delivery orifice 6;26 in the addition tube is located within the inner volume of the vessel and a check valve 7;27 is arranged in proximity of, or adjacent, the delivery orifice such that it allows flow of a fluid in the direction from the addition tube into the inner volume 3;23 and blocking flow in the reverse direction. When check valve 7;27 is arranged in proximity of delivery orifice 6;26, the distance between the check valve and the orifice may be e.g. up to 20 times the diameter of tube 5;25, such as up to 10 times, up to 5 times or up to 2 times the diameter of tube 5;25 (or the average diameter if the diameter varies along the length of tube 5;25). Short distances are advantageous due to the smaller dead volumes, but it can be easier to accommodate the check valve in the tube if some distance is allowed, When a fluid, such as a pH regulating solution, a nutrient solution, a growth factor solution or a gas is supplied to the inner volume via the addition tube and the delivery orifice, the check valve opens and when no fluid is supplied the valve is closed, blocking any convective or diffusive permeation of fluid from the inner volume into the addition tube. The vessel can typically have a volume from 0.1 litres up to several thousand litres and the diameter of the addition tube can correspondingly be from about 1 mm up to several cm. The addition tube can be connected with a port in a wall of the vessel and this port can during use of the bioreactor be connected, e.g. with tubing, to a fluid supply vessel and to a pressure-generating delivery means. The delivery means can e.g. be a pump, a pressurized fluid supply vessel or a fluid supply vessel placed above the bioreactor to generate a hydrostatic pressure. The delivery of fluid can be controlled e.g by switching or regulating a pump or by opening/closing a regulator valve in the tubing.

In some embodiments, the delivery orifice 6;26 of the addition tube is arranged to be immersed in liquid during use of the bioreactor. This has the advantage that the fluid is added directly into the cell culture liquid and there is no risk of fluid being trapped in the foam layer formed on top of the liquid during cultivation. The addition tube can e.g. be connected with a port in a top wall of the vessel and the addition tube can have a length sufficient to reach down at least halfway to a bottom wall of the vessel, such as at least 80% or at least 90% of the distance from the top wall to the bottom wall, with the delivery orifice located at or in proximity of a bottom end of the addition tube. The bioreactor should in these cases be supplied with an instruction to fill the vessel with sufficient liquid for immersion of the delivery orifice during use. The addition tube can alternatively also be connected with a port in a side wall or a bottom wall of the vessel and even in these cases the vessel should be filled with sufficient liquid for immersion of the delivery orifice during use.

In certain embodiments, the position of the delivery orifice in the vessel is adjustable. This can be achieved e.g. with a telescopic addition tube, bellows in a vessel wall port to which the addition tube is connected, etc. and has the advantage that the delivery orifice can be immersed and positioned at a point of high turbulence regardless of the degree of filling of the vessel.

In some embodiments, the delivery orifice 6;26 of the addition tube is covered by the check valve 7;27. An advantage of this is that the cell culture liquid is in direct contact with the check valve and no stagnant zones are formed outside the check valve. The check valve itself can suitably be constructed such that no stagnant zones are formed on its outside. Examples of such check valves are illustrated in FIGS. 4-7.

In some embodiments, the check valve is inserted in the addition tube, e.g. at a position in proximity of the delivery orifice.

In certain embodiments, the opening pressure of said check valve is below or equal to 10 kPa, such as between 10 Pa and 10 kPa, between 100 Pa and 10 kPa or between 1 kPa and 10 kPa. A too high opening pressure can give rise to pressure build-up and uncontrolled burst of fluid, while a too low opening pressure may cause the valve to open e.g. from pressure fluctuations induced by the agitation. The opening pressure is the minimum pressure difference between the two sides (inlet side and outlet side) of the check valve, which will cause the check valve to open. It can easily be determined with standard method, e.g. by gradually increasing the pressure on the inlet side and noting at which pressure the valve opens.

In some embodiments, the check valve comprises an elastomeric closing member 38;48;58;68. Elastomeric closing members facilitate the construction of check valves without stagnant zones and are well compatible with single use bioreactor vessels. It is also possible to have an addition tube with an integrally formed elastomeric check valve closing member, such that no separate assembly of valve parts is needed.

Figure 6:
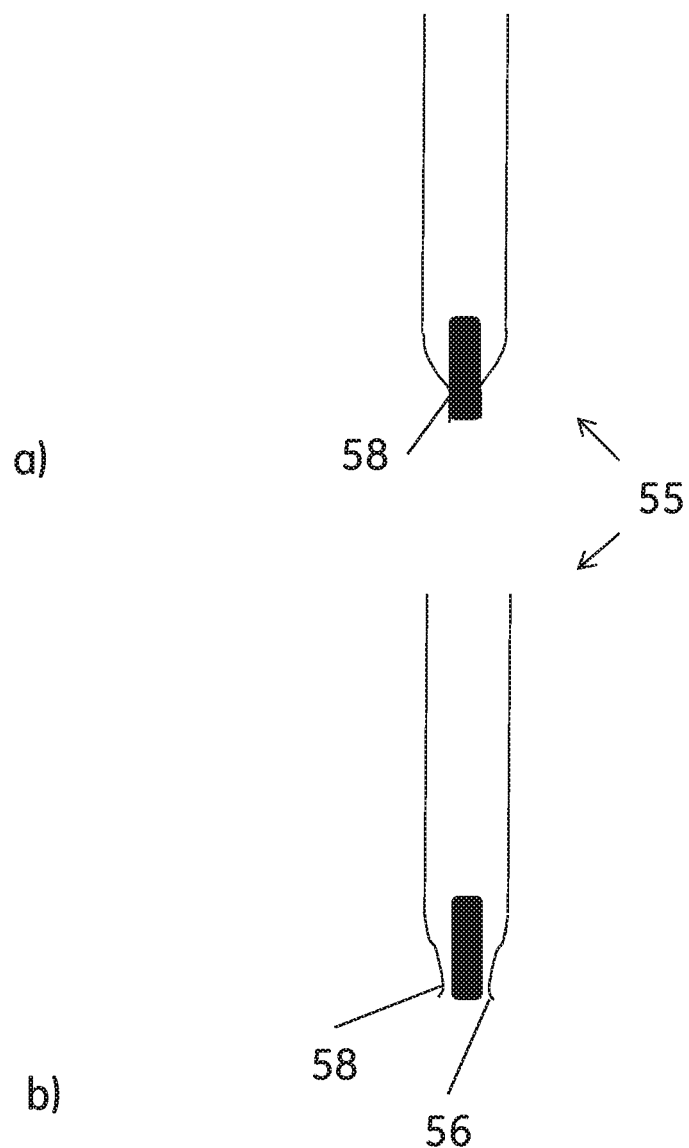
FIG. 6 shows a detailed picture of an addition tube of the invention, with a tubular check valve.
Figure 7:
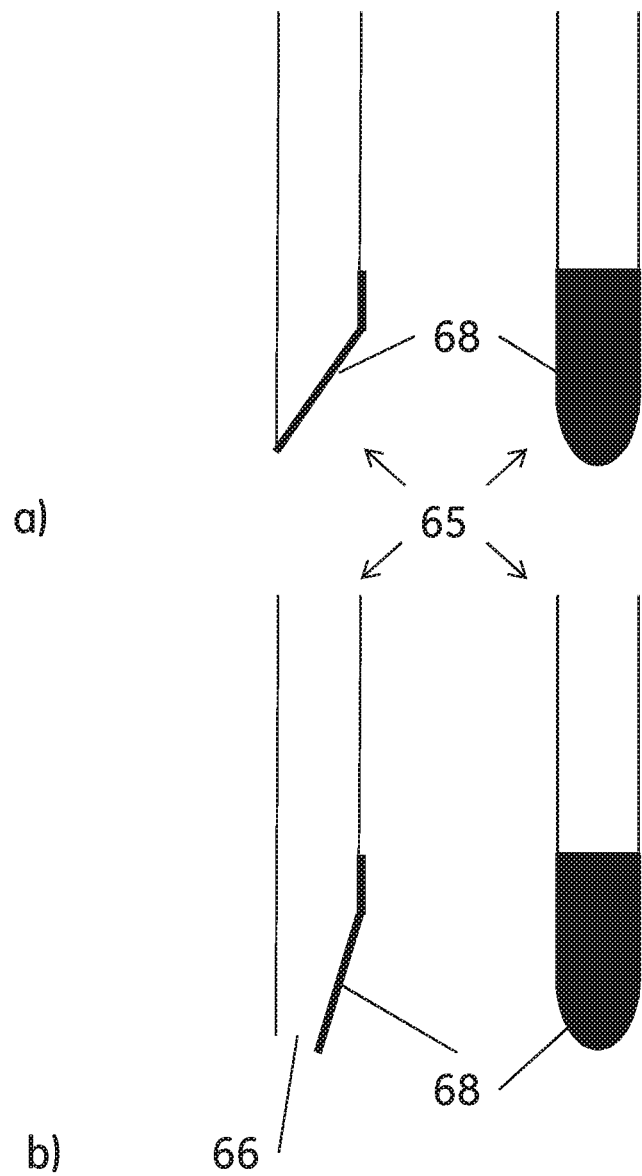
FIG. 7 shows a detailed picture of an addition tube of the invention, with a flap check valve.

In certain embodiments, the elastomeric closing member is selected from the group consisting of tubes, lips, flaps and split disks. An example of a tubular closing member 58 is shown in FIG. 6, an example of lips 48 in FIG. 5, a flap 68 in FIG. 7 and a split disk 38 in FIG. 4. All these constructions can be made with no or minimal outside stagnant zones and they are suitable for use in bioreactors.

In some embodiments, the vessel comprises a flexible plastic bag 2;22. This allows for single use bioreactors. The flexible plastic bag 2 can e.g. be supported by a rigid support structure 18 during use. The rigid support structure can be made from e.g. stainless steel.

In certain embodiments the agitation means comprises an impeller 4. The impeller is suitably located in the inner volume of the vessel and can be arranged to rotate or oscillate, e.g. by the action of an external magnetic drive.

Figure 3:
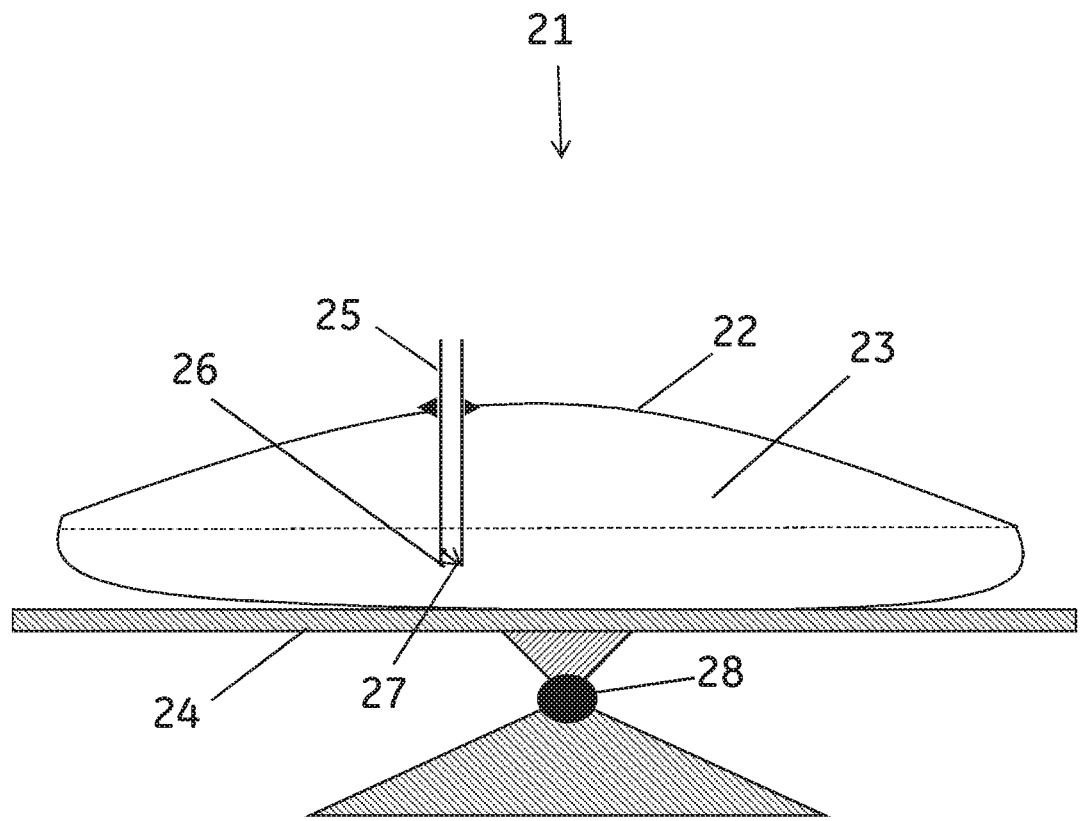
FIG. 3 shows a bioreactor according to the invention, with an inflatable bag resting on a movable platform.
Figure 4:
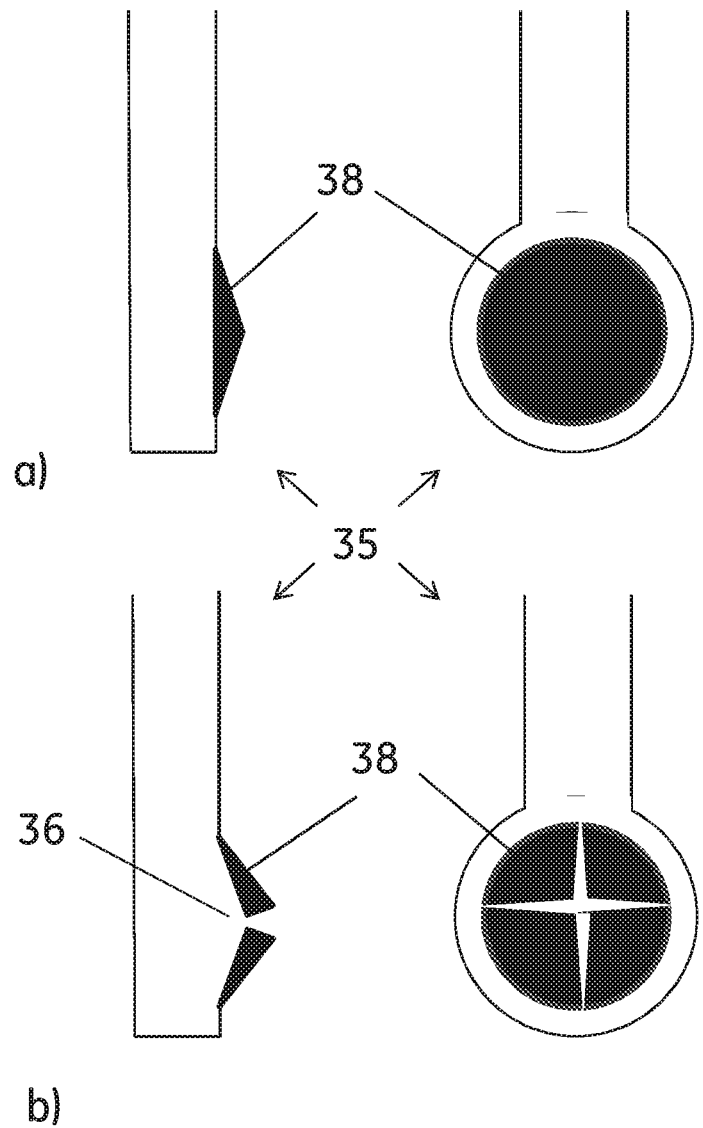
FIG. 4 shows a detailed picture of an addition tube of the invention, with a split disk check valve.
Figure 5:
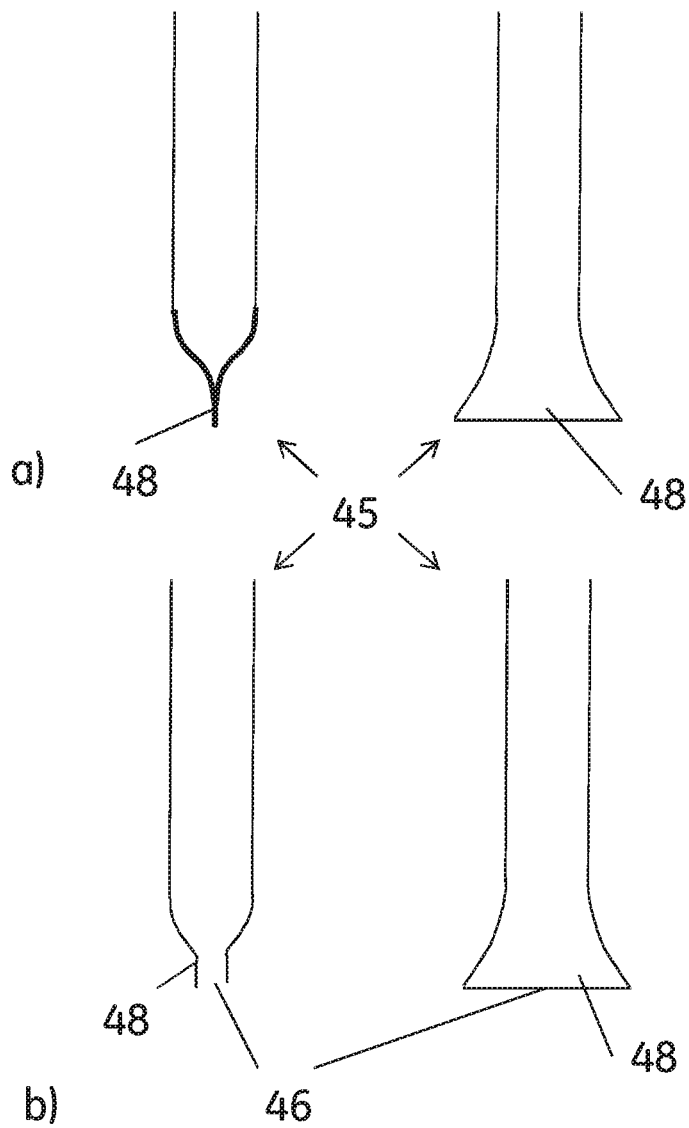
FIG. 5 shows a detailed picture of an addition tube of the invention, with a lip (duckbill) check valve.

In some embodiments the flexible plastic bag 22 is inflatable and the agitation means comprises a movable support platform 24 for the flexible plastic bag. As illustrated in FIG. 3, the inflated bag can be self-supporting and can rest on the platform 24, which can be movable around an axis 28 to generate an oscillatory rocking agitation.

In certain embodiments the bioreactor or the vessel, including the addition tube and optionally the agitation means, is radiation sterilized. This is convenient for single-use bioreactors and can be achieved when all the components are made from radiation stable materials. Suitable materials for the vessel and the addition tube can be e.g. polyethylene and ethylene copolymers, while suitable elastomers for the closing member of the check valve can be e.g. radiation stable silicones.

In some embodiments the addition tube is fluidically connected to a supply vessel containing a liquid solution comprising a pH regulator, a nutrient and/or a growth factor. The liquid solution can be e.g. aqueous ammonia for pH control, but it can also be more complex media component solutions.

In one aspect the present invention discloses a method of cell cultivation, which comprises the steps of:
a) providing a bioreactor as described above;
b) adding cell cultivation medium and cells to the inner volume of the vessel;
c) providing agitation by the agitation means, and
d) adding a liquid solution and/or a gas to the inner volume via the addition tube.

The cells can be e.g. i) animal cells, such as mammalian or insect cells, ii) microorganisms such as bacteria or yeast cells or iii) plant cells.

In certain embodiments the amount of cell cultivation medium in step b) is sufficient to immerse the delivery orifice of the addition tube.

In some embodiments the liquid solution comprises a pH regulator, a nutrient and/or a growth factor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Features from different embodiments may be combined to form new embodiments.

The invention claimed is:
1. A bioreactor comprising:
a vessel defining an inner volume configured to contain liquid contents;
an agitation means;
at least one addition tube configured to introduce reagents from outside the bioreactor, the at least one addition tube having a first end protruding into the inner volume of the vessel to be in direct contact with the liquid contents of the vessel wherein cultivation takes place and a second end residing outside of the bioreactor, the second end being opposite to the first end and higher than the first end relative to a direction of gravity; and
a check valve having a delivery orifice adjacent the first end of the at least one addition tube, with the delivery orifice configured to be in direct contact with the liquid contents of the vessel wherein cultivation takes place, the check valve comprising an elastomeric closing member covering the delivery orifice, having an opening pressure below or equal to 10 kPa for allowing flow of a fluid in a downward direction along gravity from the second end, through the addition tube and through the delivery orifice into the inner volume of the vessel and blocking flow in the reverse direction,
wherein there is no or minimal stagnant zones outside the check valve, wherein the check valve and the delivery orifice are arranged to be immersed in the liquid contents wherein cultivation takes place to fill the bioreactor, and wherein the addition tube is telescopic such that the position of the delivery orifice in the vessel is adjustable.

2. The bioreactor of claim 1, wherein the opening pressure of said check valve is between 10 Pa and 10 kPa.

3. The bioreactor of claim 1, wherein the elastomeric closing member is selected from the group consisting of tubes, lips, flaps and split disks.

4. The bioreactor of claim 1, wherein the vessel comprises a flexible plastic bag.

5. The bioreactor of claim 4, wherein the flexible plastic bag is arranged to be supported by a rigid support structure during use.

6. The bioreactor of claim 1, wherein the agitation means comprises an impeller.

7. The bioreactor of claim 4, wherein the flexible plastic bag is inflatable and the agitation means comprises a movable support platform for the flexible plastic bag.

8. The bioreactor of claim 1, wherein the addition tube is fluidically connected to a supply vessel containing a liquid solution comprising a pH regulator, a nutrient and/or a growth factor.

9. The bioreactor of claim 1, wherein the opening pressure of said check valve is between 100 Pa and 10 kPa.

10. A bioreactor comprising,
a vessel defining an inner volume configured to contain liquid contents;
an agitation means;
at least one addition tube configured to introduce reagents from outside the bioreactor, the at least one addition tube having a first end protruding into the inner volume of the vessel to be in direct contact with the liquid contents of the vessel wherein cultivation takes place; and
a check valve having a delivery orifice adjacent the first end of the at least one addition tube, with the delivery orifice configured to be in direct contact with the liquid contents of the vessel wherein cultivation takes place, for allowing flow of a fluid in a downward direction along gravity from the addition tube into the inner volume through the delivery orifice and blocking flow in the reverse direction, such that there is no or minimal stagnant zones outside the check valve,
wherein the addition tube is telescopic such that the position of the delivery orifice in the vessel is adjustable, and
wherein the check valve and the delivery orifice are arranged to be immersed in the liquid contents wherein cultivation takes place to fill the bioreactor.

11. The bioreactor of claim 1, wherein the at least one addition tube is further configured such that the first end protruding into the inner volume of the vessel is located near a bottom of the vessel.

* * * * *